United States Patent
Kising

(10) Patent No.: US 10,717,204 B2
(45) Date of Patent: Jul. 21, 2020

(54) ULTRASOUND CUTTING DEVICE

(71) Applicant: ARTECH ULTRASONIC SYSTEMS AG, Bottighofen (CH)

(72) Inventor: Juergen Kising, Kreuzlingen (CH)

(73) Assignee: Artech Ultrasonic Systems AG, Bottinghofen (CH)

( * ) Notice: Subject to any disclaimer, the term of this patent is extended or adjusted under 35 U.S.C. 154(b) by 199 days.

(21) Appl. No.: 14/274,688

(22) Filed: May 10, 2014

(65) Prior Publication Data
US 2014/0249555 A1 Sep. 4, 2014

Related U.S. Application Data

(63) Continuation-in-part of application No. PCT/EP2012/004663, filed on Nov. 9, 2012.

(51) Int. Cl.
*B26D 7/08* (2006.01)
*B26D 7/26* (2006.01)
*A61B 17/32* (2006.01)
*A61B 17/22* (2006.01)
*B26D 5/00* (2006.01)
*B26D 1/00* (2006.01)

(52) U.S. Cl.
CPC ...... *B26D 7/086* (2013.01); *A61B 17/320068* (2013.01); *B26D 5/00* (2013.01); *B26D 7/2614* (2013.01); *A61B 17/22004* (2013.01); *A61B 17/22012* (2013.01); *A61B 2017/320072* (2013.01); *B26D 2001/006* (2013.01)

(58) Field of Classification Search
CPC ........... A61B 17/320068; A61B 2017/320072; A61B 17/22012; A61B 17/22004; A61F 9/00745; B26D 5/00; B26D 7/2614; B26D 2001/006; B26D 7/086; A61C 3/03
See application file for complete search history.

(56) References Cited

U.S. PATENT DOCUMENTS

| | | | | |
|---|---|---|---|---|
| 2,984,241 A | * | 5/1961 | Carlson | A61B 17/1604 30/277 |
| 5,026,387 A | * | 6/1991 | Thomas | A61B 17/320068 310/316.01 |
| 5,057,182 A | * | 10/1991 | Wuchinich | B06B 3/00 156/580.1 |
| 5,171,387 A | * | 12/1992 | Wuchinich | B06B 3/00 156/580.1 |
| 5,828,156 A | * | 10/1998 | Roberts | B06B 3/00 310/317 |
| 5,862,728 A | * | 1/1999 | Giamello | A21C 15/04 83/13 |
| 5,897,523 A | * | 4/1999 | Wright | A61B 17/320068 600/459 |

(Continued)

FOREIGN PATENT DOCUMENTS

| | | |
|---|---|---|
| DE | 43 10 832 | 10/1994 |
| DE | 44 21 465 | 12/1995 |
| DE | 10 2007 014 635 | 9/2008 |

*Primary Examiner* — Jing Rui Ou
(74) *Attorney, Agent, or Firm* — Klaus J. Bach

(57) ABSTRACT

In an ultrasound cutting device comprising an ultrasound transducer connected to a generator and provided with a sound conductor which is connected to a cutting blade and extends along a line which deviates from a straight line, the generator includes means for running the ultrasound waves in a controlled manner through a predetermined frequency range.

2 Claims, 8 Drawing Sheets

(56) References Cited

U.S. PATENT DOCUMENTS

| | | | | |
|---|---|---|---|---|
| 5,897,569 | A | * | 4/1999 | Kellogg ......... A61B 17/320068 310/316.01 |
| 6,058,823 | A | | 5/2000 | Michoud |
| 2001/0004695 | A1 | * | 6/2001 | Vercellotti ......... A61B 17/1688 606/79 |
| 2002/0072034 | A1 | * | 6/2002 | Hickok .................... A61C 3/03 433/119 |
| 2004/0023187 | A1 | * | 2/2004 | Hickok .................... A61C 3/03 433/119 |
| 2004/0030254 | A1 | * | 2/2004 | Babaev .......... A61B 17/320068 600/459 |
| 2011/0196286 | A1 | * | 8/2011 | Robertson ...... A61B 17/320068 604/22 |

* cited by examiner

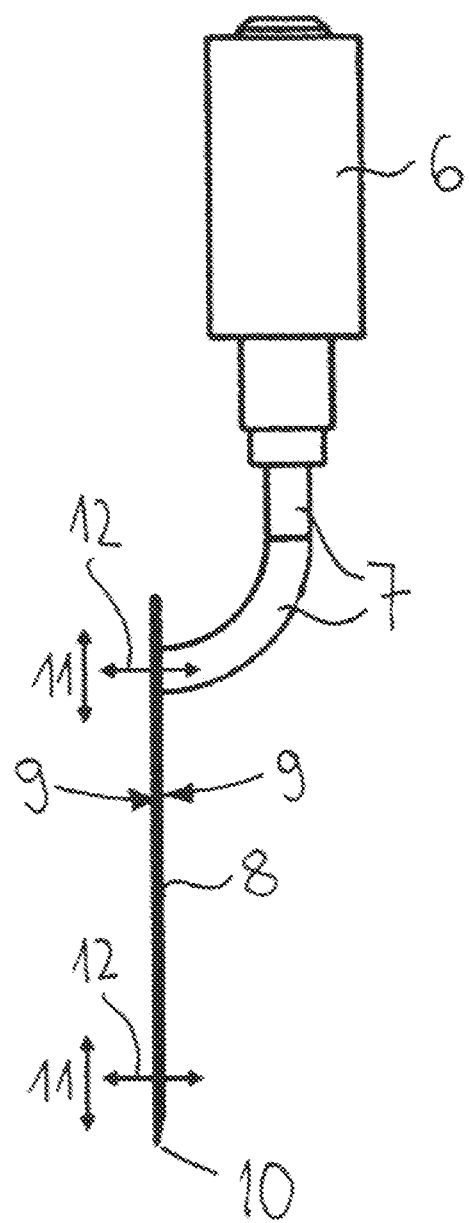
Fig. 2

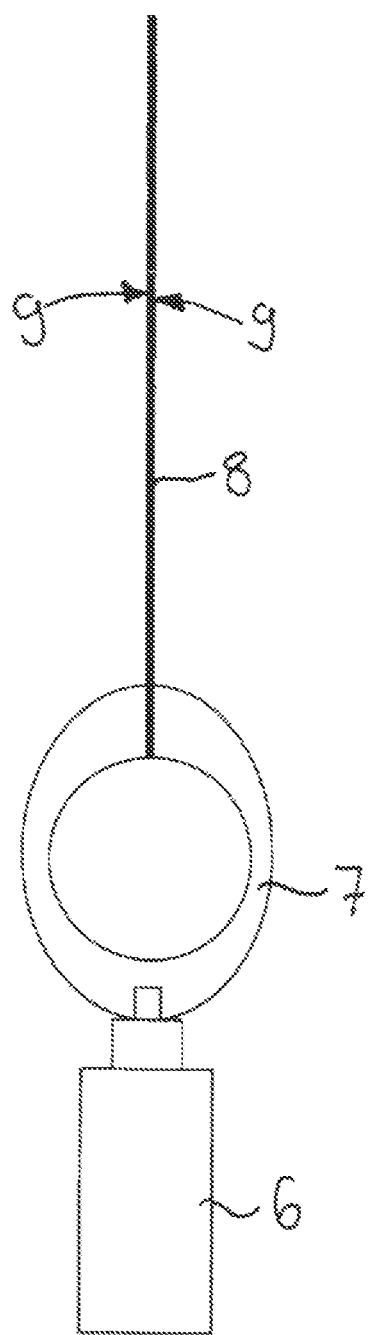
Fig. 5

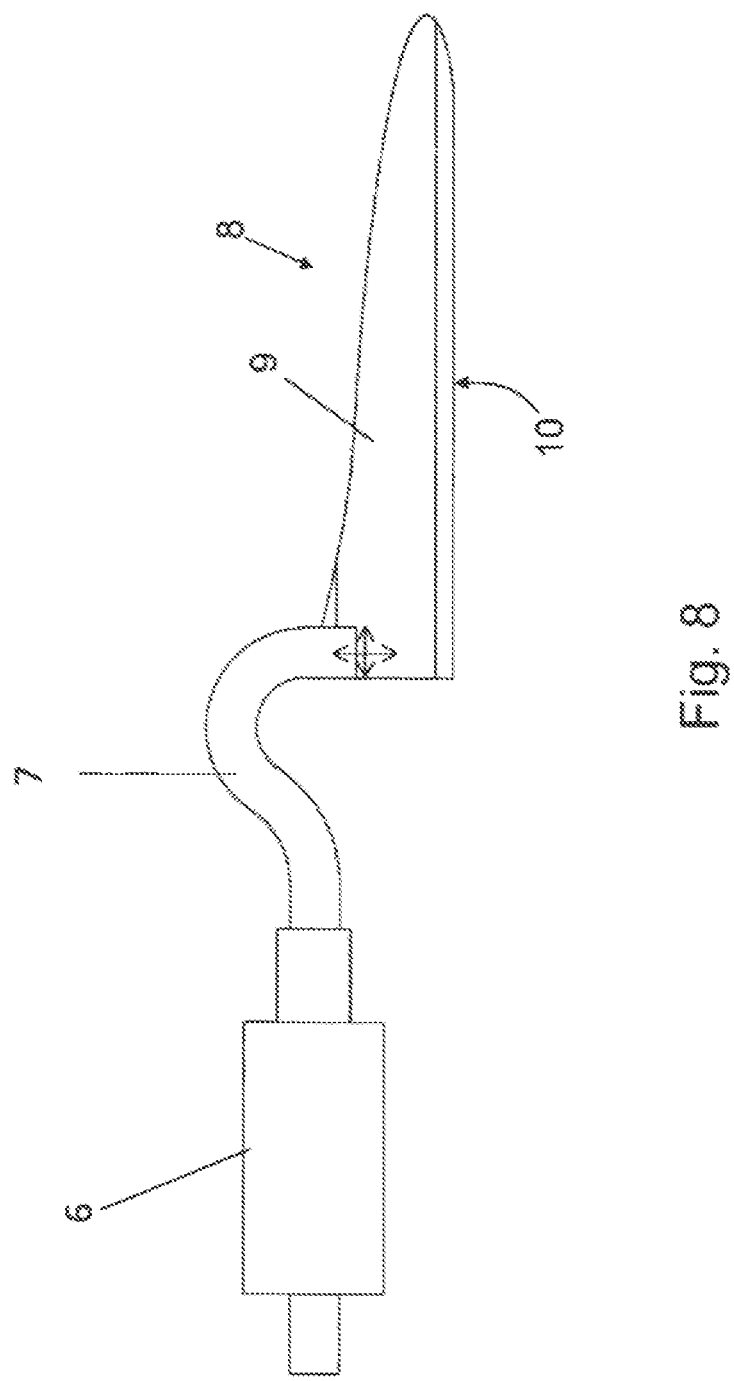

ULTRASOUND CUTTING DEVICE

This is a Continuation-In-Part application of International patent application PCT/EP2012/004663 filed Nov. 9, 2012 and claiming the priority of German patent application 10 2011 118 208.3 filed Nov. 11, 2013.

BACKGROUND OF THE INVENTION

The invention resides in an ultrasound cutting device with at least one ultrasound transducer, at least one sound conductor and at least one cutting blade, wherein the sound conductor is arranged between the ultrasound transducer the cutting blade so as to interconnect the two and wherein the longitudinal center axis of the sound conductor extends along a line which deviates from a straight line.

Such an ultrasound cutting device for cutting food items such as baked products, cheese, fish or similar products to be cut, is known from DE 43 19 832 A1. The cutting device disclosed therein comprises a cutting blade which extends essentially in a plane and which is connected at its end remote from the blade tip to a sound conductor forming therewith a single piece. A section of the sound conductor spaced from the cutting blade is threaded to an ultrasound transducer so that the ultrasound oscillations can be coupled into the sound conductor in the longitudinal direction of that cutting blade. Between the ultrasound transducer and the cutting blade, the sound conductor includes a 90° bend with a predetermined radius of curvature which extends in a plane normal to the plane in which the cutting blade is disposed and in the longitudinal direction of the cutting blade. At the end, which is connected to the cutting blade, the curved area converges toward the cutting blade Inc continuously differentiable manner. Via a course which deviates from the straight line of the sound conductor, the sound conductor is excited to vibrate in the longitudinal direction of the cutting blade as well as in a plane extending normal to the plane of the cutting blade. Herein, the vibration component in a direction normal to the plane of the cutting blade provides for a reduction of the friction between the flanks of the cutting blade and the product to be cut. Still, during cutting a certain amount of friction will occur, which limits the cutting speed. It has also been found that the cutting blade is subjected by the ultrasound vibrations at different locations to different mechanical loads.

It is therefore the object of the present invention to provide an ultrasound cutting device of the type described above, which is of a compact design but nevertheless has a high cutting speed and facilitates a uniform mechanical stress of the cutting blade.

SUMMARY OF THE INVENTION

In an ultrasound cutting device comprising an ultrasound transducer connected to a generator and provided with a sound conduct or which is connected to a cutting blade and extends along a line which deviates from a straight line, the generator includes means for running the ultrasound waves in a controlled manner through a predetermined frequency range.

With this design, the nodal points of the ultrasound waves on the cutting blade are not stationary but change their position with the vibration frequency.

In this way, a sticking or adhering of the cutting blade to the product being cut is prevented. With the frequency variation, also the mechanical load on the cutting blade is reduced since large resonance amplitudes occur only for short periods, so that a pulse-like excitation is obtained as a result, which has been found to be advantageous for the cutting procedure since, in this way, the product is shaken off the blade. The frequency variation provides for the excitation of different blade geometries and the use of several ultrasound transducers in connection with a particular generator so that very wide cutting knives can be provided. The course of the sound conductor which deviates from a straight line can be so selected that the cutting blade can be excited in such a way that it vibrates in ultrasound vibration directions which extend transversely to one another. In this way, plate waves can be coupled into the cutting blade which can extend between the side surfaces which are parallel to one another and/or extend wedge-like toward the cutting edge of the cutting blade. The plate waves have a component which is oriented longitudinally in the plane defined by the cutting blade as well as a component which is oriented transverse to this plane. This is advantageous for the cutting procedure, since the product being cut is subjected to an impulse acting sidewardly, that is transverse, with respect to the plane of the cutting blade which results in a better release of the product or material being cut from the cutting blade. On the other hand, the cutting blade is also excited to vibrate in the direction of the cutting blade plane, preferably in the longitudinal direction of the cutting blade. In this way, during the cutting procedure, the friction is reduced so that the ultrasound energy coupled into the cutting blade is utilized better for the cutting procedure. With the plate waves, the cutting blade can be comparatively large without the need to provide slots in the cutting blade. This permits a relatively inexpensive blade design. There are practically no restrictions as far as the geometry of the cutting blade is concerned.

Although DE 10 2007 014 635 A1 discloses an arrangement for the ultrasound excitation of structures which include an ultrasound transducer connected to a generator and means for passing through a predetermined ultrasound frequency range, this arrangement has no cutting blade. Rather, the arrangement is provided for an ultrasound excitation of several sieves which have different resonance frequencies.

The sound conductor is preferably curved. Herein, the direction in which the sound conductor extends may change by at least 45°, particularly at least by 60 degrees and possibly by at least 75°, preferably however by 90°.

In an advantageous embodiment of the invention, the cutting blade is a laminar element and the sound wave conductor is in the form of a guide rod which is connected to the cutting blade in a direction transverse to the plane in which the cutting blade extends. The plate waves in the cutting blade can be better excited in this way. The cutting blade may have surfaces which extend parallel or concentrically with respect to each other and/or side surfaces which extend in a wedge-like manner.

In an expedient embodiment of the invention, the sound conductor has an annular shape wherein a first end area of the sound conductor is connected to the ultrasound transducer and a second end area of the sound conductor which is disposed diametrically opposite the first end area is connected to the cutting blade. In this way, the ultrasound can be coupled into the cutting blade symmetrically from two sides. The sound conductor which is disposed in a plane has preferably an annular or oval shape. But it may also be rectangular.

The cutting blade may also be cylindrical wherein the sound wave conductor is connected to the cutting blade at the outer cylinder surface thereof. Herein, under a cylindrical sound conductor, a laminar sound conductor is to be understood which extends along an area which is generated by moving a curve extending in a plane along a straight line which is not disposed in this plane. The straight line may extend normal to the plane (straight cylinder) or inclined with respect to the plane (aslant cylinder).

In a particular embodiment of the invention, the cutting blade is of circular or oval shape. With such a cutting blade, rod-like objects can for example be cut out of a solid material.

However, the cutting blade may also have corners, for example it may have a rectangular shape. Such a cutting blade permits for example the cutting of prism-shaped objects from a body of material.

In an advantageous embodiment, the ultrasound cutting device includes several ultrasound transducers which are connected each via at least one sound conductor to sound-coupling locations of the cutting blade which are spaced from one another.

In a further development of the invention, the sound conductor is formed integrally with the cutting blade and is in the form of a knife shaft which is preferably U-shaped. This arrangement provides for a particular simple and robust design for an ultrasound cutting device.

Below the invention will be described on the basis of exemplary embodiments with reference to the accompanying drawings.

BRIEF DESCRIPTION OF THE DRAWINGS

FIG. 2 is a side view of the ultrasound cutting device shown in FIG. 1, FIG. 5 is a top view of an ultrasound cutting device in which the cutting blade is connected to an ultrasound transducer by way of an oval sound conductor, FIG. 8 is a side view of an ultrasound cutting device wherein the ultrasound waves are coupled into the cutting blade from the top.

DESCRIPTION OF EXEMPLARY EMBODIMENTS

Figure 1:
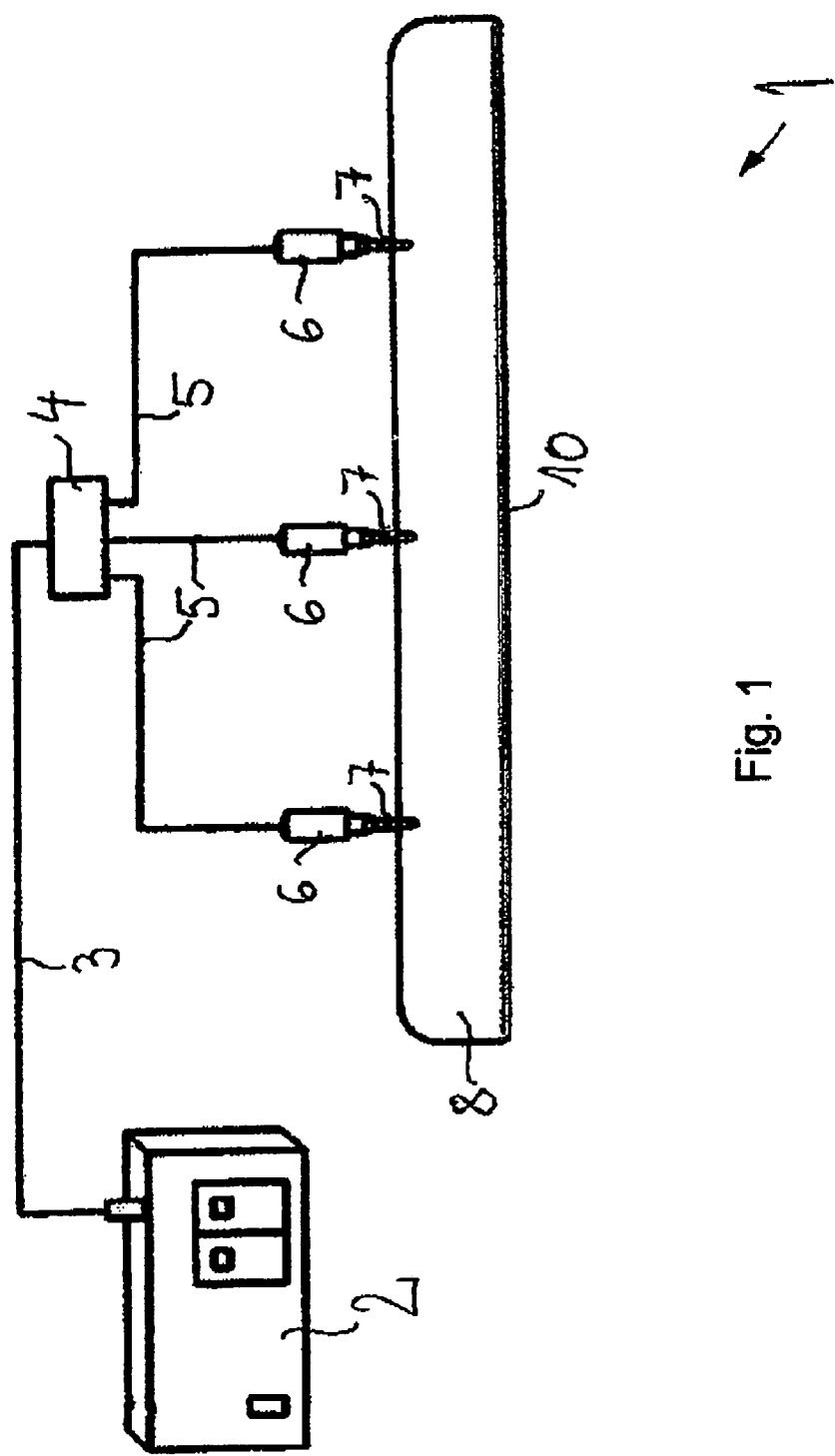
FIG. 1 is a front view of an ultrasound cutting device which includes a straight blade which is excited with the aid of several ultrasound transducers.

In FIG. 1, the numeral 1 indicates overall an ultrasound cutting device which includes an ultrasound generator 2 which is provided with means for running through a predetermined ultrasound frequency range (sweep function). The generator 2 is connected is a first high frequency cable 3 to an inlet connection of a distributor 4. The distributor 4 has three output connections, each connected by means of a second high frequency cable 5 to a high frequency input of an ultrasound transducer 6.

Each ultrasound transducer 6 is connected to a particular coupling location of a cutting blade 8. As shown in FIGS. 1 and 2, the cutting plate 8 is in the form of a thin plate, which has two side surfaces 9 which extend parallel to each other and of which one is firmly connected to the sound conductors 7. At its lower edge area, the cutting blade 8 thins out wedge-like toward a cutting edge 10. However, other configurations are possible wherein the cutting blade becomes thinner toward the cutting edge 10 over its whole height.

FIG. 2 shows that the sound conductor 7 has a curved section which is disposed in a plane extending normal to the longitudinal axis of the cutting blade 8 and parallel to the drawing plane of FIG. 2. The curved sound conductor section 7 has a curvature of about 90° and is connected at its end facing the side surface 9 to the cutting blade 8 by means of a welding joint which is not shown in the drawing. At its opposite end remote from the cutting blade 8, the curved sound conductor section is connected to the respective ultrasound transducer 6 via a straight sound conductor section which couples vibrations into the end of the sound conductor 7 which is remote from the cutting blade 8 in a direction normal to the longitudinal axis of the cutting blade.

It is pointed out however that the sound conductor 7 may also have other configurations which deviate from a straight line such as an S- or L-shaped sound conductor configuration With the sound conductor 7 in the form of a curved conductor rod, the cutting blade 8 excited in a direction normal to the longitudinal axis of the cutting blade 8 which is in the drawing plane of FIG. 2 as well as in the direction of the line of intersection of this plane with the plane in which the cutting blade 9 extends as shown by the double arrows 11 as well as in a direction normal to the plane in which the cutting blade 8 extends as indicated by the double arrows 12.

For determining the energy supplied from the generators 2 to the ultrasound transducers 6, the ultrasound cutting device 1 includes a measuring arrangement which is not shown in the drawings. The measuring arrangement is in communication via a control arrangement with the means for running through the predetermined ultrasound frequency range. Originally, a first scan is performed wherein, starting with a predetermined start-out value, the ultrasound frequency is changed up to a predetermined end value. The start-out value may for example be 30 kHz and the end value about 38 kHz.

During running through the ultrasound frequency range the energy output of the generator 2 is measured as a function of the ultrasound frequency. Thereafter, by means of a microprocessor the frequency point $f_o$ is determined at which the highest energy output is provided. This frequency point is stored. Then the smallest frequency value $f_{min}$ and the largest frequency band are determined which, with an adjustable bandwidth of for example up to 4000 Hz is provided preferably symmetrically about the frequency point $f_o$. The smallest frequency value may for example be $f_{min}=f_o-2000$ Hz and the largest frequency value may be $f_{max}=f_o+2000$ Hz. The generator 2 is first so controlled that the cutting blade 8 is excited with the lowest frequency value $f_{min}$. Thereafter the frequency is increased in each case by a predetermined value of for example 1 Hz for exciting the cutting blade 8 at the respective new frequency.

After each increase of the frequency, it is examined whether the new frequency is smaller than the earlier determined largest frequency value $f_{max}$. If this is the case, the earlier mentioned steps comprising the increase of the frequency, the excitation of the cutting blade 8 with this frequency and the examination whether the new frequency is smaller than the largest frequency $f_{max}$ are repeated.

If the new frequency is not smaller than the largest frequency $f_{max}$ the frequency is reduced in each case by a predetermined amount and the cutting blade 8 is excited with the newly obtained frequency value.

After each reduction of the frequency, it is examined whether the new frequency is larger than the previously determined smallest frequency value $f_{min}$. If this is the case, the above-mentioned steps comprising a reduction of the frequency, the excitation of the cutting blade 8 by this frequency and the examination whether the new frequency is larger than the smallest frequency $f_{min}$ is repeated.

If the new frequency is not larger than the smallest frequency the above mentioned steps are repeated starting with the smallest frequency value $f_{min}$.

The user can adjust the bandwidth in which this sweep is performed between 200 Hz and 4000 Hz. The value of the step width may also be greater than 1 Hz. By adjustment of the bandwidth, the cutting result may be optimized in order to counteract a drifting of the resonance point by temperature influences or coupling variations, a new scan is initiated after regular periods as performed originally at the initiation of the cutting procedure in order to re-establish the resonance point $f_o$.

However, this new scan is not performed on the whole range from 30 to 38 kHz, but only immediately around the resonance point $f_o$ in order to avoid to generate dead times since the new scan can be performed at a lower energy.

Figure 3:
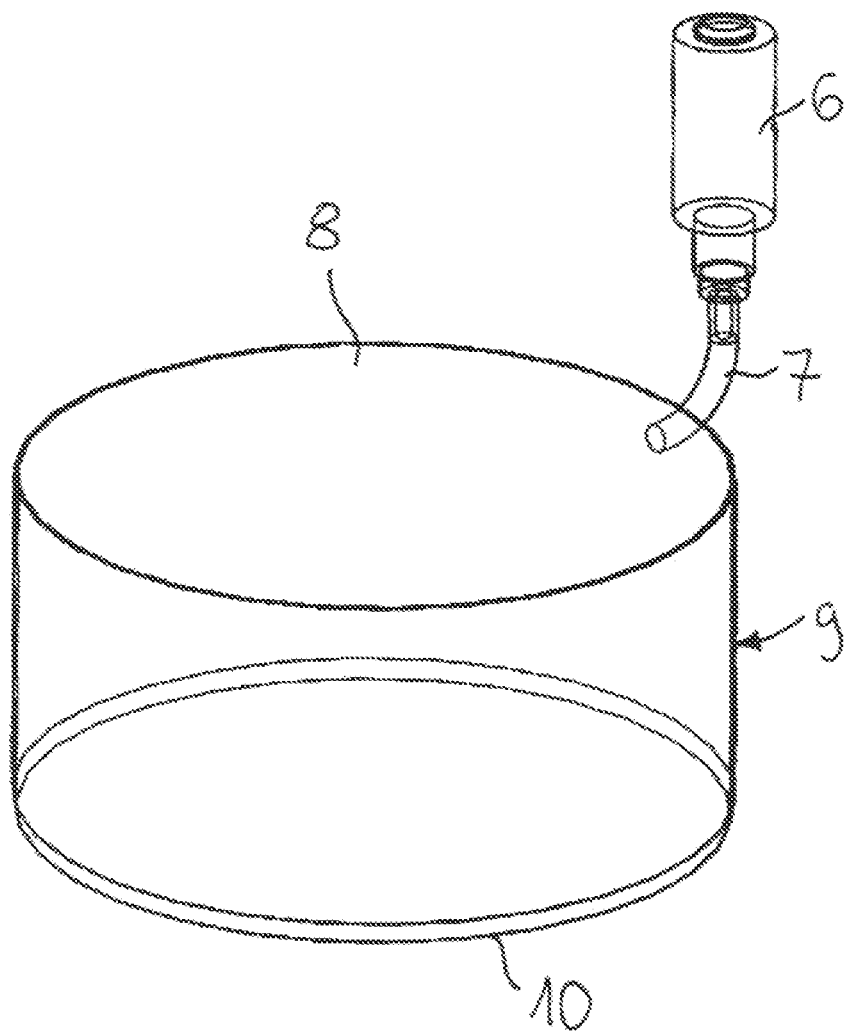
FIG. 3 shows an ultrasound cutting device including a circular cutting blade.
Figure 3:
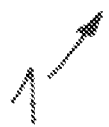
Figure 4:
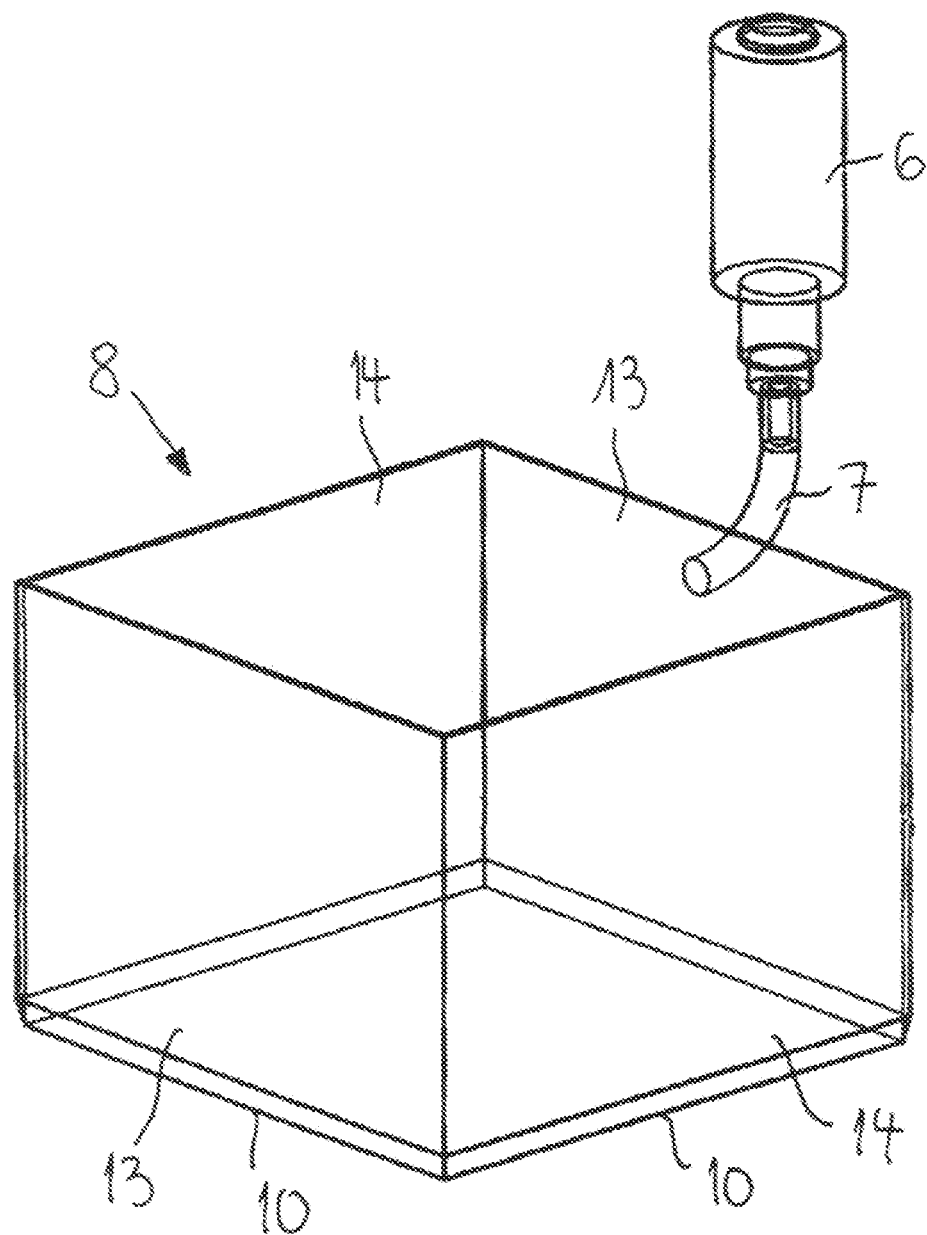
FIG. 4 shows an ultrasound cutting device including a rectangular on blade.

In the exemplary embodiments as shown in FIGS. 3 and 4, the cutting blade 8 is essentially cylindrical. In the exemplary embodiment of FIG. 3, the cutting blade 8 is formed by a thin-walled circular cylindrical tube which becomes thinner wedge-like in its lower edge area toward the cutting edge 10. The ultrasound energy is coupled into this cutting blade via a curved sound conductor 7, whose geometry corresponds essentially to that of the sound conductor 7 shown in FIG. 2. The in-coupling location is spaced from the cutting edge 10 and arranged at the upper edge area of the cutting blade 8. However, the in-coupling location also be arranged elsewhere at the cutting blade 8, for example, in the lower edge area near the cutting edge 10.

In the exemplary embodiment shown in FIG. 4, the cutting edge 10 has a rectangular shape. It is clearly shown that the cutting edge 8 has two parallel first cutting blade sections 13 and two second parallel cutting blade sections 14 which extend transversely to the first cutting blade sections 13. The first cutting blade sections 13 and the second cutting blade sections 14 are each in the form of thin planar plates which, at their lower ends, are wedge-shaped toward the cutting edges 10 thereof.

The first cutting blade sections 13 are connected to the second cutting blade sections 14 in a box-like manner. The ultrasound is coupled into the blade arrangement again via a curved sound conductor 7 whose geometry corresponds essentially to that of the sound conductor 7 as shown in FIG. 2. The in-coupling location is remote from the cutting edge at the upper edge area of the cutting blade 8.

In the exemplary embodiment as shown in FIG. 5, the sound conductor 7 has an oval shape. Here the plane in which the sound conductor 7 is disposed extends at a right angle to the plane in which the plate-shaped cutting blade 8 is arranged. The cutting edge 10 of the cutting blade 8 extends essentially parallel to the plane in which the sound conductor 7 is disposed.

A first end area of the sound conductor 7 is connected to the ultrasound transducer 6 and the second end area diametrically opposite the first end area is connected to the cutting blade 8. The ultrasound transducer 6 is arranged in line with the cutting blade 8 and couples the ultrasound waves into the sound conductor 7 in the longitudinal direction of the cutting blade 8.

Figure 6:
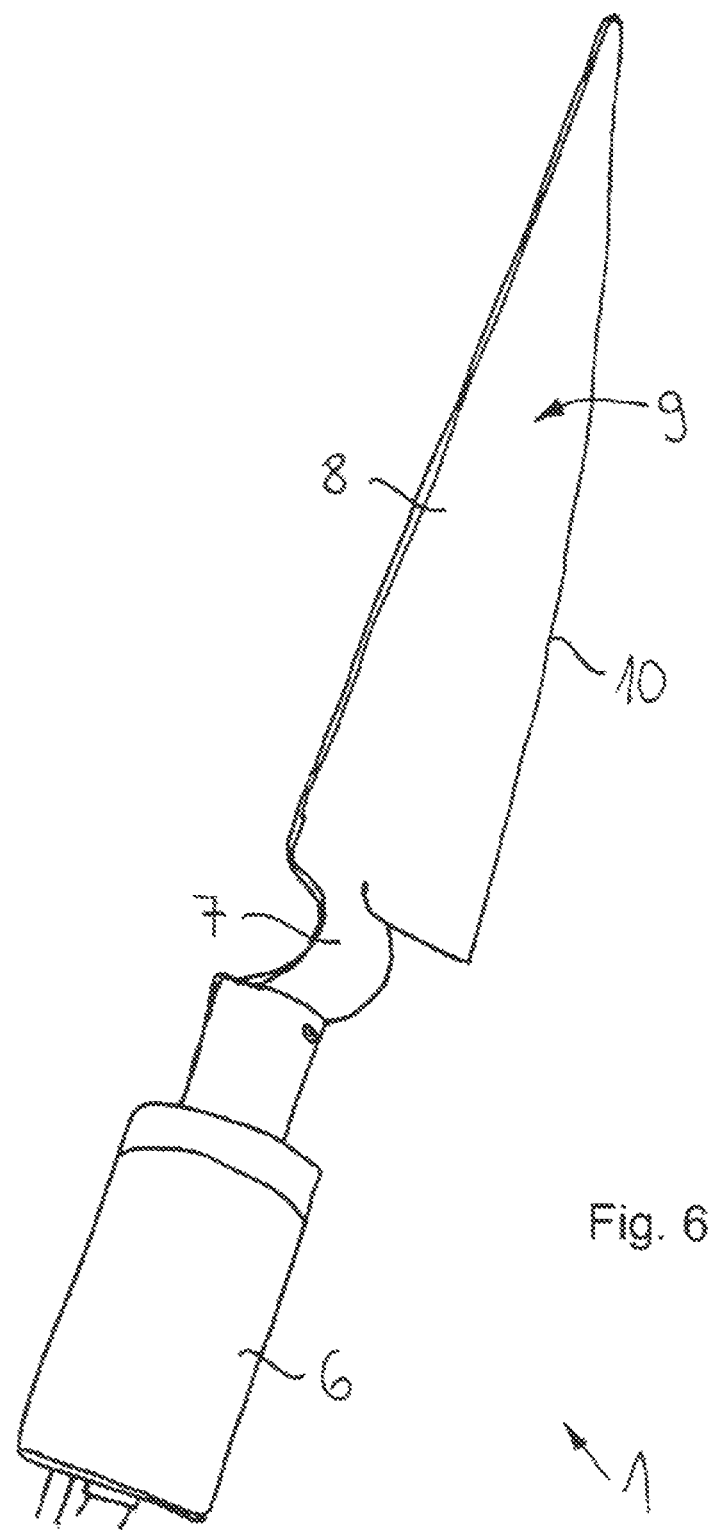
FIGS. 6 and 7 are side views of an ultrasound cutting device with blade onto which a sound conductor is integrally formed.
Figure 7:
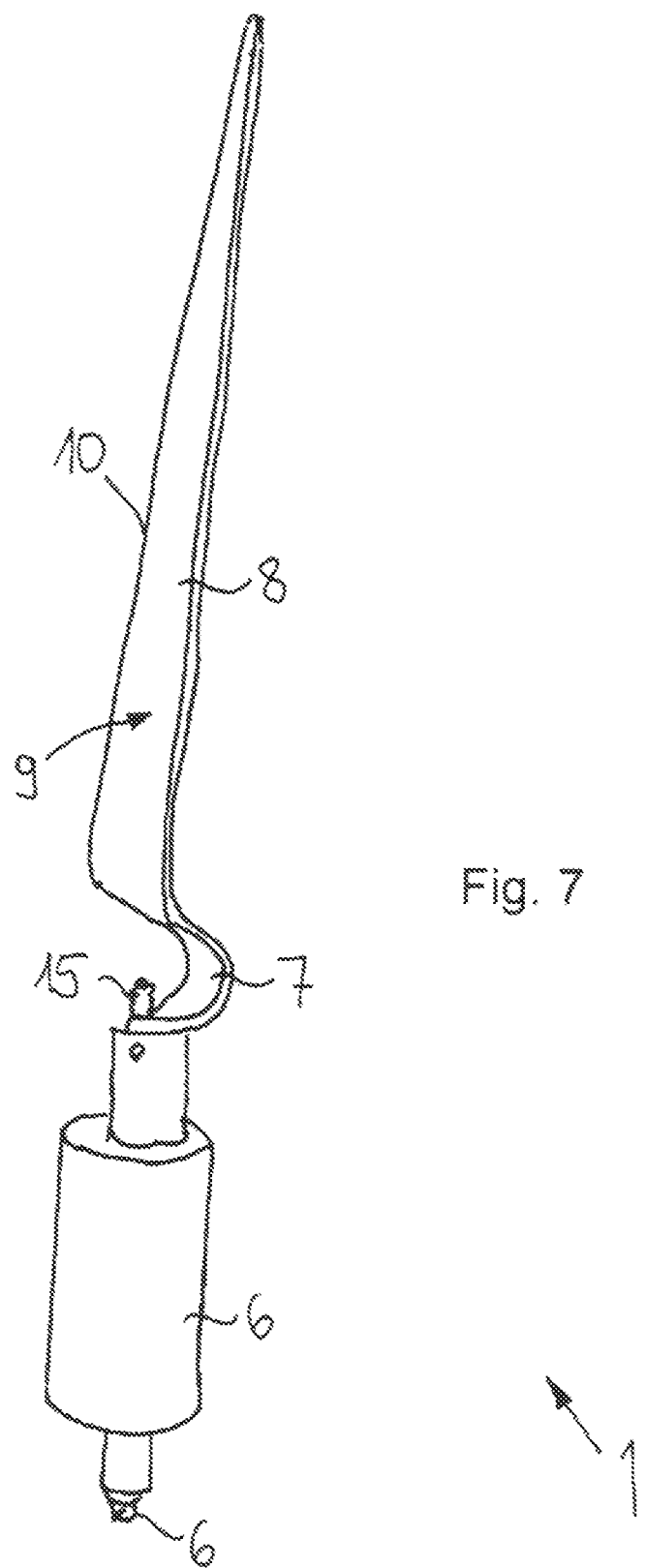

In the exemplary embodiment as shown in FIGS. 6 and 7, the cutting blade 8 is in the form of a thin planar plate, which becomes thinner, wedge-like, toward the cutting edge 10 preferably over the full height of the cutting blade 8. The height of the cutting blade 8 becomes continuously greater toward the sound conductor 7 starting from the end of the cutting blade 8 remote from the sound conductor 7.

The sound conductor 7 is an integral part of the cutting blade 8 and forms the blade shaft or, respectively, the hilt of the cutting blade 8. In a plane extending normal to the cutting blade 8 and parallel to the longitudinal axis of the cutting blade 8, the hilt is U-shaped. The sound conductor 7 has an about rectangular cross-section. At its free end remote from the cutting blade 8, the sound conductor 7 is connected to the ultrasound transducer 6 by means of a screw 15.

In this exemplary embodiment as shown in FIG. 8, the cutting blade 8 is connected to the sound conductor 7 at the back and of the cutting blade opposite the cutting edge 10. As a result, the ultrasound waves are coupled into the cutting blade 8 from the top thereof. It is clearly shown that the end area of the sound conductor 7 facing the cutting blade 8 extends about normal to the cutting edge 10. Herein the sound conductor 7 is curved in the plane, in which the plate-shaped blade 8 is disposed, so as to extend in opposite directions forming a U-bend therebetween. The ultrasound converter 6 is oriented with its longitudinal axis extending parallel to the cutting edge 10.

What is claimed is:

1. An ultrasound cutting device (1) comprising at least two ultrasound transducers (6) connected to an ultrasound generator (2), each ultrasound transducer provided with a sound conductor (7) connected to a cutting blade (8), and each sound conductor (7) being arranged between each ultrasound transducer (6) and the cutting blade (8) so as to interconnect each ultrasound transducer (6) and the cutting blade (8), each sound conductor (7) having a longitudinal center axis which extends along a line which deviates from a straight line, and the ultrasound generator (2) having a sweep function for running ultrasound waves to the cutting blade (8) through a predetermined ultrasound frequency range, wherein the cutting blade (8) is in the form of a planar element extending in a plane and each sound conductor (7) is in the form of an ultrasound guide rod which is curved near the cutting blade and is connected to the cutting blade at sound in-coupling locations of the cutting blade (8) which are spaced from one another, all sound conductors (7) being curved so as to extend at the sound in-coupling locations transverse to the plane in which the cutting blade (8) extends.

2. An ultrasound cutting device according to claim 1, wherein the ultrasound generator (2) is adapted to supply its maximum power to the ultrasound transducers (6) at an ultrasound frequency which is in the middle between the highest and the lowest frequency of the ultrasound frequency range through which the generator (2) runs.

* * * * *